United States Patent [19]

Akhavan-Tafti

[11] Patent Number: 5,552,298
[45] Date of Patent: Sep. 3, 1996

[54] ENZYME-CATALYZED CHEMILUMINESCENCE FROM HYDROXYARYL CYCLIC DIACYLHYDRAZIDE COMPOUNDS

[75] Inventor: Hashem Akhavan-Tafti, Sterling Heights, Mich.

[73] Assignee: Lumigen, Inc., Southfield, Mich.

[21] Appl. No.: 965,231

[22] Filed: Oct. 23, 1992

[51] Int. Cl.$^6$ .............................. C12Q 1/28; G01N 33/53
[52] U.S. Cl. .................... 435/28; 435/6; 435/7.9; 435/8; 435/21; 435/966; 435/968; 436/172; 436/501; 436/819
[58] Field of Search .................. 435/28, 6, 7.9, 435/7.91–92, 8, 18–19, 21, 966, 968; 436/501, 172, 819

[56] References Cited

U.S. PATENT DOCUMENTS

| | | | |
|---|---|---|---|
| 4,612,712 | 9/1986 | Baldwin | 435/4 |
| 4,794,073 | 12/1988 | Dattagupta et al. | 435/6 |
| 4,834,918 | 5/1989 | Wulff et al. | 252/700 |
| 4,842,997 | 6/1989 | Carter et al. | 435/6 |
| 4,853,327 | 9/1989 | Dattagupta | 435/6 |
| 4,857,652 | 8/1989 | Schaap | 549/510 |
| 4,950,588 | 9/1990 | Dattagupta | 435/6 |

FOREIGN PATENT DOCUMENTS

| | | | |
|---|---|---|---|
| 2237383 | 5/1991 | United Kingdom | 435/6 |

OTHER PUBLICATIONS

I. E. Kalinichenko, A. T. Pilipenko, V. A. Barovskii, Ukr. Khim. Zh. (Russ. Ed.), 43(10), 1102–6 (1977).

Kalinichenko, I. E., Barovskii V. A., Pilipenko, A. T., Ukr. Khim. Zh. (Russ. Ed.), 44(7), 748–52 (1978).

A. T. Pilipenko, V. A. Barovskii, I. E. Kalinichenko, Zh. Anal. Khim. 33(10), 1880–4 (1978).

Krika et al. "Bioluminescent and Chemiluminescent Detection of Horseradish Peroxidase Labels in Ligand Binder Assays," *Luminescence Immunoassays and Molecular Applications*, Ch. 6, . 77–98, 1990.

Thorpe et al. "Phenols as Enhancers of the Chemiluminescent Horseradish Peroxidase–Lumind–Hydrogen Peroxide Reaction: Applications in Luminescence–Monitored Enzyme Immunoassays", *Clinical Chemistry*, V. 31 N. 8; pp. 1335–1341. 1985.

Wurzberg et al, "A Pulse Radiolysis Study of the Chemiluminescence of Some Luminol–Like Molecules", *The Journal of Physical Chemistry*. V. 83 N. 21, pp. 2687–2692. Oct. 18, 1979.

Kalinichenko et al. "Comparison of Spectra, Intensity and Quantum Yield of Chemiluminescence in Reactions of Substituted Phthalic hydrazides with different Oxidizing Agents", *Ukr. Khim. Zh.* (Russian Edition) v. 43 N. 10, pp. 1102–1106. 1977.

Heinicke et al; "Quantitative dot–blot assay for proteins using enhanced chemiluminescence"; J. Imm. Meth. 152(1992) 227–236.

Mize et al; "Dual–Enzyme Cascade—An amplified method for the detection of alkaline phosphate"; Anal Biochem., 179; 229–235 (1989).

Pollard–Knight; "Nonradioactive DNA detection on Southern blots by enzymatically triggered chemiluminescence"; Anal. Biochem. 185, 353–58 (1990).

Conyers, S. M., et al., Analytical Biochemistry 192 207–211 (1991).

Akhavan–Tafti, H., et al., Bioluminescence and Chemiluminescence 199–202 (1994).

Cercek, B., et al., J. Biolumin Chemilumin. 9 273–277 (1994).

Vlasenko, S. B., et al., J. of Bioluminescence and Chemiluminescence 4 164–176 (1989).

Egorov, A. M., et al., Chemiluminescent and Bioluminescent Assays 186–290 (1993).

Whitehead, T. P., et al., Bioluminescence and Chemiluminescence, 425–429 (1993).

I. E. Kalinichenko, V. A. Barovskii, Ikr. Khim. Zh. (Russ. Ed.), 45(1), 58–62 (1979).

I. E. Kalinichenko, T. M. Tkachuk, A. T. Pilipenko, Zh. Anal. Khim., 39(7), 1281–4 (1984).

R. B. Brundett, D. F. Roswell, E. H. White, J. Am. Chem. Soc., 94, 7536 (1972).

J. De Boever, F. Kohen and D. Vandekerckhove in Bioluminescence and Chemiluminescence New Perspectives, J. Scholmerich, et al, Eds., J. Wiley & Sons, Chichester, pp. 257–260 (1987).

T. P. Whitehead, G. H. Thorpe, T. J. Carter, C. Groucutt, L. J. Kricka, Nature, 305, 158 (1983).

H. R. Schroeder, P. O. Vogelhut, R. J. Carrico, R. C. Boguslaski, R. T. Buckler, Anal. Chem.48 1933(1976).

H. R. Schroeder in Luminescent Immunoassays: Perspectives in Endocrinology and Clinical Chemistry, M. Serio and M. Pazzagli, Eds., Raven Press, New York, pp. 129–146 (1982).

M. Pazzagli, G. Messeri, A. L. Caldini. G. Monetti, G. Martinazzo, M. Serio, J. Steroid Biochem., 19, 407 (1983).

G. H. Thorpe, L. J. Kricka, S. B. Mosely, T. P. Whitehead, Clin. Chem., 31, 1335 (1985).

A. P. Schaap, R. S. Handley, B. P. Giri, Tetrahedron Lett., 935 (1987).

A. P. Schaap, T. S. Chen,R. S. Handley, R. DeSilva, B. P. Giri, Tetrahedron Lett., 1155 (1987).

A. P. Schaap, M. D. Sandison, R. S. Handley, Tetrahedron Lett., 1159 (1987).

(List continued on next page.)

*Primary Examiner*—Robert Warden
*Assistant Examiner*—Christopher Y. Kim
*Attorney, Agent, or Firm*—Ian C. McLeod

[57] ABSTRACT

An assay method, compositions and test kits using a hydroxyaryl cyclic diacylhydrazide is described. A hydrogen peroxide and peroxidase enzyme. The preferred compositions incorporate enhancer compounds and a chelating agent which suppresses light production prior to addition of a peroxidase enzyme. The assay method can test for a peroxidase enzyme, a peroxide or can be used in immunoassays and probe assays.

30 Claims, 5 Drawing Sheets

OTHER PUBLICATIONS

Y. Omote, H. Yamamoto, and N. Sugiyama, Chem. Commun., 914 (1970).

A. P. Schaap, H. Akhavan, L. J. Romano, Clin. Chem., 35, 1863 (1989).

D. Pollard–Knight, A. C. Simmonds, A. P. Schaap, H. Akhavan, M. A. W. Bradley, Anal. Biochem. 185, 353–358 (1990).

J. M. Clyne, J. A. Running, R. Sanchez–Pescador, D. Besemer, M. Stempien, A. P. Schaap, R. S. Stephens, M. S. Urdea, J. Biolumin.Chemilumin. 2, 193 (1988).

K. Tanabe, T. Kawasaki, M. Maeda, A. Tsuji, M. Yabuuchi, Bunseki Kagaku, 36, 82 (1987).

A. Tsuji, M. Maeda, H. Arakawa, Anal. Sci., 5, 497 (1989).

K. Sasamoto, Y. Ohkura, Chem. Pharm. Bull. 38(5), 1323 (1990).

K. Sasamoto, Y. Ohkura, Chem. Pharm. Bull. 39(2), 411 (1991).

R. Hauber, R. Geiger, Nuc. Ac. Res., 16(32), 1213 (1988).

G. H. Thorpe, S. B. Mosely, L. J. Kricka, R. A. Stott, T. P. Whitehead, Anal. Chim. Acta, 170, 107 (1985).

J. A. Matthews, A.Batki, C. Hynds, L. J. Kricka, Anal. Biochem., 151, 205 (1985).

A. K. Campbell, Ellis Harwood, Chemiluminescence Chichester, England 80 and 441, 446–450, 457 (1988).

R. A. W. Stott and L. J. Kricka in Bioluminescence and Chemiluminescence, New Perspectives, J. Scholmerich, et al., Eds., J. Wiley and Sons, Chichester, pp. 237–240 (1987).

Bronstein, B. Edwards, J. C. Voyta, J. Biolumin. Chemilumin. 4, 99–111 (1989).

K.–D. Gundermann, W. Horstmann, G. Bergman, Lieb. Ann. der Chem., 684, 127–141 (1965).

ENZYME-CATALYZED CHEMILUMINESCENCE FROM HYDROXYARYL CYCLIC DIACYLHYDRAZIDE COMPOUNDS

BACKGROUND OF THE INVENTION

(1) State of the Invention

This invention relates to a method of generating light (chemiluminescence) by the action of a peroxidase enzyme with an oxidant such as hydrogen peroxide on a group of hydroxyaryl cyclic diacylhydrazides. The invention also relates to a method of greatly increasing the amount of chemiluminescence produced from this process by the use of specific enhancers. The invention also relates to the use of this method to detect the peroxidase enzyme. The invention also relates to the use of this method to detect hydrogen peroxide. Further, the invention relates to the use of the method to detect and quantitate various biological molecules. For example, the method may be used to detect haptens, antigens and antibodies by the technique of immunoassay, proteins by Western blotting, DNA and RNA by Southern and Northern blotting, respectively. The method may also be used to detect DNA in DNA sequencing applications. The method may additionally be used to detect enzymes which generate hydrogen peroxide such as glucose oxidase, glucose-6-phosphate dehydrogenase, galactose oxidase, galactose-6-phosphate dehydrogenase, and amino acid oxidase.

(2) Prior Art a. Chemiluminescent Oxidation of Hydroxyaryl Cyclic Diacylhydrazides. A series of publications have appeared concerning the chemiluminescent reactions of the hydroxyphthalhydrazides, 5- and 6-hydroxy-2,3-dihydrophthalazine-1,4-dione with different chemical oxidizing agents (I. E. Kalinichenko, A. T. Pilipenko, V. A. Barovskii, Ukr. Khim. Zh. (Russ. Ed.), 43(10), 1102–6 (1977); Kalinichenko, I. E.; Barovskii, V. A.; Pilipenko, A. T., Ukr. Khim. Zh. (Russ. Ed.), 44(7), 748–52 (1978); A. T. Pilipenko, V. A. Barovskii, I. E. Kalinichenko, Zh. Anal. Khim., 33(10), 1880–4 (1978); I. E. Kalinichenko, V. A. Barovskii, Ukr. Khim. Zh. (Russ. Ed.), 45(1), 58–62 (1979); I. E. Kalinichenko, T. M. Tkachuk, A. T. Pilipenko, Zh. Anal. Khim., 39(7), 1281–4 (1984)). Gundermann reports the chemiluminescent oxidation of 7-hydroxynaphthalene-1,2-dicarboxylic hydrazide in aqueous solution with hydrogen peroxide and a metal catalyst (K.-D. Gundermann, W. Horstmann, G. Bergman, Lieb. Ann. der Chem., 684, 127–141 (1965)). No publications are known concerning the use of hydroxyaryl cyclic diacylhydrazides with a peroxidase enzyme to generate chemiluminescence. Further, there are no known reports of the use of hydroxyaryl cyclic diacylhydrazides to generate chemiluminescence for the detection of biological compounds.

b. Chemiluminescent Oxidation of Luminol and Related Compounds. Aminoaryl cyclic diacylhydrazides such as luminol and isoluminol react with hydrogen peroxide and a peroxidase enzyme catalyst (such as horseradish peroxidase, HRP) under basic conditions with emission of light. The reaction is also catalyzed by small amounts of several metal ions including Fe(III), Cu(II) and Cr(III) or iron-containing organic compounds (e.g. R. B. Brundett D. F. Roswell, E. H. White, J. Am. Chem. Soc., 94, 7536 (1972)). This reaction has been used as the basis for analytical methods for the detection of hydrogen peroxide and for metal ions. Luminol and isoluminol may be directly conjugated to a species to be detected. The first chemiluminescent immunoassay using luminol as a label was reported by Schroeder for an assay of biotin. (H. R. Schroeder, P. O. Vogelhut, R. J. Carrico, R. C. Boguslaski, R. T. Buckler, Anal. Chem. 48, 1933 (1976). Several applications of the use of luminol derivatives as labels have been reported since then (H. R. Schroeder in Luminescent Immunoassays: Perspectives in Endocrinology and Clinical Chemistry, M. Serio and M. Pazzagli, Eds., Raven Press, New York, pp 129–146 (1982); M. Pazzagli, G. Messeri, A. L. Caldini, G. Monetti, G. Martinazzo, M. Serio, J. Steroid Biochem., 19, 407 (1983); J. De Boever, F. Kohen and D. Vandekerckhove in Bioluminescence and Chemiluminescence New Perspectives, J. Scholmerich, et al, Eds., J. Wiley & Sons, Chichester, pp 257–260 (1987)). Various enhancers have also been employed in conjunction with the use of luminol to increase the intensity of light emitted. These include D-luciferin (T. P. Whitehead, G. H. Thorpe, T. J. Carter, C. Groucutt, L. J. Kricka, Nature, 305, 158 (1983)) and p-iodophenol and p-phenylphenol (G. H. Thorpe, L. J. Kricka, S. B. Mosely, T. P. Whitehead, Clin. Chem., 31, 1335 (1985)). U.S. Pat. No. 4,834,918 to Wulff et al describes the use of fluorescein as an enhancer.

c. Enzyme-Catalyzed Chemiluminescent Reactions (1) Enzymatic Triggering of Stabilized 1,2-Dioxetanes. Recently developed thermally stable dioxetanes can be triggered by chemical and enzymatic processes to generate chemiluminescence on demand (A. P. Schaap, U.S. Pat. No. 4,857,652; A. P. Schaap, R. S. Handley, B. P. Giri, Tetrahedron Lett., 935 (1987); A. P. Schaap, T. S. Chen, R. S. Handley, R. DeSilva, B. P. Giri, Tetrahedron Lett., 1155 (1987); and A. P. Schaap, M. D. Sandison, R. S. Handley, Tetrahedron Lett., 1159 (1987); Bronstein, B. Edwards, J. C. Voyta, J. Biolumin. Chemilumin. 4, 99–111 (1989); A. P. Schaap, H. Akhavan, L. J. Romano, Clin. Chem., 35, 1863 (1989); D. Pollard-Knight, A. C. Simmonds, A. P. Schaap, H. Akhavan, M. A. W. Bradley, Anal. Biochem. 185,353–358 (1990); J. M. Clyne, J. A. Running, R. Sanchez-Pescador, D. Besemer, M. Stempien, A. P. Schaap, R. S. Stephens, M. S. Urdea, J. Biolumin. Chemilumin. 2, 193 (1988)).

(2) Enzymatic Generation of Hydrogen Peroxide. Various enzymatic reaction schemes are known which produce hydrogen peroxide. The generated hydrogen peroxide can, in turn, be used to oxidize a compound which emits light. For example, glucose oxidase reacts with $O_2$ and sucrose to produce hydrogen peroxide. Similarly, amino acid oxidase reacts with an amino acid and $O_2$ to produce hydrogen peroxide. Examples of compounds which are oxidized by hydrogen peroxide to produce light are luminol and isoluminol, lucigenin, esters of N-methylacridine and esters and amides of oxalic acid. Glucose-6-phosphate dehydrogenase and galactose-6-phosphate dehydrogenase have been used to produce $H_2O_2$ indirectly by reduction of oxygen through an electron-relay system. (K. Tanabe, T. Kawasaki, M. Maeda, A. Tsuji, M. Yabuuchi, Bunseki Kagaku, 36, 82 (1987), A. Tsuji, M. Maeda, H. Arakawa, Anal. Sci., 5, 497 (1989)).

(3) Enzymatic Generation of Luminol from a Luminol-NAG Conjugate. The compound o-aminophthalhydrazide-N-acetyl-β-D-glucosaminide (luminol-NAG) and 4'-(6'-diethylaminobenzofuranyl)-phthalhydrazide-N-acetyl-β-D-glucosaminide are substrates for the enzyme N-acetyl-β-D-glucosaminidase which serve as a masked form of luminol. Upon action of the enzyme on these substrates, luminol or a luminol derivative are liberated which may be detected as described above. (K. Sasamoto, Y. Ohkura, Chem. Pharm. Bull. 38(5), 1323 (1990); K. Sasamoto, Y. Ohkura, Chem. Pharm. Bull. 39(2), 411 (1991)).

(4) Bioluminescent Detection of Firefly or Bacterial Luciferase. A class of enzymes known as luciferases, catalyze the autoxidation of certain substrates known as luciferins in a number of living organisms. An example is the firefly whose bioluminescent process oxidizes its luciferin to produce light with 88% efficiency. A DNA dot-hybridization assay has been reported in which alkaline phosphatase was employed to generate free firefly luciferin from the phosphate salt. Luciferase added in the final step caused the chemiluminescent oxidation of the luciferin (R. Hauber, R. Geiger, Nuc. Ac. Res., 16(32), 1213 (1988)).

d. Use of Chemiluminescence in Enzyme Immunoassays and DNA Hybridization assays. Biological assays such as enzyme immunoassays and DNA probe assays involving enzymes utilize a wide variety of substrates which either form a color (chromogenic), become fluorescent (fluorogenic) or emit light (chemiluminogenic) upon reaction with the enzyme. Of these three choices, chemiluminescence offers the greatest sensitivity. In an assay, the enzyme (reporter enzyme) is conjugated or bound to the molecule to be detected or to some other substance capable of selectively binding or associating with the molecule to be detected. Once the bound reporter enzyme is separated from unbound enzyme, a substrate is provided with which the reporter enzyme generates a signal. Chemiluminogenic substrates used to date include enzyme-triggerable dioxetanes such as the alkaline phosphatase substrate LUMIGEN PPD (A. P. Schaap, H. Akhavan, L. Y. Romano, Clin. Chem., 35, 1863 (1989)). This substrate has been used extensively in enzyme-linked immunoassays and DNA probes. The enzyme horseradish peroxidase has been widely used in enzyme immunoassays and DNA hybridization assays with chemiluminescent detection using luminol or isoluminol as substrate (T. P. Whitehead, G. H. Thorpe, T. J. Carter, C. Groucutt, L. J. Kricka, Nature, 305, 158 (1983), G. H. Thorpe, L. J. Kricka, S. B. Mosely, T. P. Whitehead Clin. Chem., 31, 1335 (1985), G. H. Thorpe, S. B. Mosely, L. J. Kricka, R. A. Stott, T. P. Whitehead Anal. Chim. Acta, 170, 107 (1985), J. A. Matthews, A. Batki, C. Hynds, L. J. Kricka, Anal. Biochem., 151, 205, (1985)). A general discussion appears in Chemiluminescence, A. K. Campbell, Ellis Harwood, Chichester, England 80 and 441, 446–450, 457 (1988). Commercially available kits for conjugation of HRP with enhanced luminol chemiluminescent detection are sold under the tradename AMERLITE.

OBJECTS

It is therefore an object of the present invention to provide a method and hydroxyaryl cyclic diacylhydrazides for use in generating chemiluminescence by the action of a peroxidase enzyme for the detection of biological materials and compounds. It is also an object of the present invention to provide a method and hydroxyaryl cyclic diacylhydrazides for use in generating chemiluminescence by the action of a peroxidase enzyme for the detection of enzymes and enzyme-conjugates which produce hydrogen peroxide. Additionally, it is an object of the present invention to provide a method and hydroxyaryl cyclic diacylhydrazides for use in generating chemiluminescence by the action of a peroxidase enzyme for use in enzyme-linked immunoassays and nucleic acid assays in solution and on surfaces.

IN THE DRAWINGS

FIG. 8 shows the result of a DNA dot blot analysis of biotinylated lambda DNA/Hind III fragments with chemiluminescent detection using horseradish peroxidase (HRP) and a phthalhydrazide of the present invention. Shown are dot blots on (FIG. 8A) nitrocellulose and (FIG. 8B) polyvinylidene difluoride (Immobilon-P™) membrane of 15 ng of DNA detected with avidin-HRP and a reagent composition containing 5-hydroxy-2,3-dihydrophthalazine-1,4-dione and p-iodophenol. The two columns of spots on the left in both FIGS. 8A and 8B represent dilutions of biotinylated lambda DNA/Hind III fragments containing 150 ng of herring sperm DNA. The control spots are only 150 ng of herring sperm DNA.

GENERAL DESCRIPTION

The present invention relates to a process for producing chemiluminescence which comprises reacting a hydroxyaryl cyclic diacylhydrazide with a peroxide compound and a peroxidase enzyme.

Further, the present invention relates to an improvement in a method for detecting an analyte in an assay procedure by a chemiluminescent reaction, the improvement which comprises: providing a reagent composition which generates light in the presence of a peroxidase which comprises: a hydroxyaryl cyclic diacylhydrazide; a phenolic compound which enhances light production from the acylhydrazide and decreases background chemiluminescence in the absence of peroxidase; a peroxide compound which reacts with the acylhydrazide in the presence of the peroxidase; a chelating agent which prevents the peroxide compound from activating the acylhydrazide prior to the addition of the peroxidase to the composition; and a nonionic surfactant which acts to enhance the light production; and adding a peroxidase to the reagent composition so that light is produced for detecting the analyte.

Finally, the present invention relates to a kit for detecting an analyte in an assay procedure by a chemiluminescent reaction to produce light which comprises in separate containers: a hydroxyaryl cyclic diacylhydrazide in a reagent composition and a peroxidase enzyme, wherein the light is detected in the assay procedure by reacting the reagent composition with the peroxidase.

The detection of chemiluminescence from the oxidation of a hydroxyaryl cyclic diacylhydrazide by a peroxide, preferably sodium perborate, catalyzed by a peroxidase enzyme can be accomplished with good sensitivity. Enhancement of this reaction by incorporation of chemiluminescence-enhancing substances has permitted the measurement of chemiluminescence using still lower levels of the peroxidase enzyme. Coupling the peroxidase enzyme to a biological molecule of interest then permits the detection of this biological molecule with great sensitivity.

A key consideration in developing ultrasensitive detection systems is to provide the largest signal possible through amplification while maintaining the lowest possible level of background signal in relation to the signal to be measured. For this purpose, additives, such as EDTA, have been discovered which suppress the generation of chemiluminescence from the reaction of hydrogen peroxide and hydroxyaryl cyclic diacylhydrazides in the absence of peroxidase enzymes.

The present invention involves a method of generating chemiluminescence from the oxidation of hydroxyaryl cyclic diacylhydrazides by the action of a peroxidase enzyme, a peroxide compound and enhancers. The invention also relates to the use of this method to detect the peroxidase enzyme with high sensitivity. Further, the invention relates to the use of the method to detect and quantitate various biological molecules which are bound to this enzyme by chemical bonds or through physical interactions. The intensity of the resulting chemiluminescence provides a direct measure of the quantity of labeled organic or biological molecule. For example, the method may be used to detect haptens, antigens and antibodies by the technique of immunoassay, proteins by Western blotting, DNA and RNA by Southern and Northern blotting, respectively. The method may also be used to detect DNA in DNA sequencing applications.

The preferred hydroxyaryl cyclic diacylhydrazides are:

Structures I and II are known compounds and are made by reaction of the corresponding anhydride or dialkyl ester with hydrazine. Compounds III and IV can be made by the reaction of hydrazine with the appropriate dimethyl or diethyl ester. Several methods appear in the chemical literature for preparing the diethyl ester precursor to compound III. Compound IV is described in *Liebigs Annalen der Chemie*, 684, 127 (1965). Compound IV is chemiluminescent when oxidized with hydrogen peroxide and heme.

The following is the preferred Scheme:

Scheme 1

-continued
Scheme 1

The method may be used to detect hydrogen peroxide generated by enzymatic reactions. It is well known that several enzymes including glucose oxidase, glucose-6-phosphate dehydrogenase, galactose oxidase, galactose-6-phosphate dehydrogenase, and amino acid oxidase produce hydrogen peroxide during the oxidation of their native substrates. It is shown that the method of the present invention may also therefore be used as a means to detect the enzymes mentioned above which generate hydrogen peroxide. Glucose oxidase has been used as a label enzyme in enzyme immunoassays and as a reporter molecule in glucose sensing devices.

An important part of the invention is that a hydroxyaryl cyclic diacylhydrazide, a peroxide compound, a phenolic compound and a chemiluminescence background suppressing agent may be combined in one solution and stored for later use without generating a large background chemiluminescence signal. This would not be expected in view of the fact that the combination of a hydroxy-substituted aryl cyclic diacylhydrazide and certain oxidants normally constitute a highly chemiluminescent reaction system.

An unexpected finding of the present invention is that incorporation of certain substituted phenol compounds in combination with nonionic surfactants into the reaction mixture enhances the chemiluminescence produced in the presence of added peroxidase. This is surprising in view of the fact that the substrate diacylhydrazide is itself also a phenol. A second phenol would not a priori be expected to affect any enhancement. Phenolic compounds found to enhance the amount of chemiluminescence produced in the reaction of hydroxyaryl cyclic diacylhydrazide with a peroxide compound and a peroxidase enzyme include but are not limited to: p-phenylphenol, p-iodophenol, p-bromophenol, p-hydroxycinnamic acid and 6-bromo-2-naphthol, for instance.

The invention relates to a method for generating chemiluminescence by the action of a peroxidase enzyme or enzyme conjugate with a mixture containing a hydroxyaryl cyclic diacylhydrazide, a peroxide compound, an enhancer or catalyst and a suppressing agent in an aqueous buffer. The invention also relates to the use of the method for the detection of biological molecules such as haptens, antigens and antibodies in immunoassays. The invention also relates to the use of the method for the detection on solid supports such as nitrocellulose, nylon or polyvinylidene difluoride (PVDF) membranes, of proteins in Western blots, DNA in Southern blots and other DNA hybridization assays and RNA in Northern blots.

The present invention involves a solution in an aqueous buffer containing 1) a phenol enhancer, 2) a peroxide compound wherein the peroxide compound may be hydrogen peroxide, urea peroxide, or a perborate salt, 3) 5-hydroxy-2,3-dihydrophthalazine-1,4-dione, 4) a cation complexing agent wherein the agent may be selected from the group consisting of chelating agents such as ethylenediaminetetraacetic acid (EDTA) diethylenetriaminepentaacetic acid (DTPA), or ethylenebis(oxyethylenenitrilo)-tetraacetic acid (EGTA) and their salts, and 5) a nonionic surfactant such as polyoxyethylenated alkylphenols, polyoxyethylenated alcohols, polyoxyethylenated ethers, polyoxyethylenated sorbitol esters and the like. It is anticipated that various hydroxyaryl cyclic diacylhydrazides may also be useful in practicing the present invention.

In a preferred method of practicing the present invention an aqueous buffer solution with a pH in the range of 8–10 containing 5-hydroxy-2,3-dihydrophthalazine-1,4-dione at a final concentration from about 0.01M to $1\times10^{-4}$M, a phenol compound such as p-phenylphenol at a final concentration from about 0.01M to $1\times10^{-6}$M and a nonionic surfactant at a final concentration from about 1% to 0.01% (v/v) is mixed with a second solution in water or aqueous buffer containing a peroxide source such as hydrogen peroxide or preferably a perborate salt and a cation complexing agent such as EDTA at a final concentration from about $1\times10^{-3}$M to $1\times10^{-6}$M to form the detection reagent solution. This solution is contacted with the peroxidase enzyme which may either be in solution or attached to a solid support. Optimum concentrations of reagents must be determined individually for each composition. The concentration of enhancer in particular should be optimized with care for each different enhancer used in order to produce the maximum enhancement of light emission.

Significant advantages of hydroxyaryl cyclic diacylhydrazides and compositions of the present invention containing them is their stability toward thermal, hydrolytic and photochemical degradation and ease of purification. Aminoaryl cyclic diacylhydrazides such as luminol and compositions containing them are readily decomposed by room light (Y. Omote, H. Yamamoto, and N. Sugiyama, Chem. Commun, 914 (1970)) leading to loss of sensitivity and poor reproducibility when used in chemiluminescence detection schemes. Aminoaryl cyclic diacylhydrazides are difficult to prepare and maintain in a state of high purity and must either be protected from light or purified immediately before use (R. A. W. Stott and L. J. Kricka in Bioluminescence and Chemiluminescence, New Perspectives, J. Scholmerich, et al., Eds., J. Wiley and Sons, Chichester, pp 237–240 (1987)). Hydroxyaryl cyclic diacylhydrazides can be purified to a high degree by recrystallization and maintain their purity without special storage requirements. A particular advantage of the present invention is that aqueous solutions of 5-hydroxy-2,3-dihydrophthalazine-1,4-dione retain their activity after storage at ambient temperature and in room light for at least two months.

When using the method of this invention as a means to detect hydrogen peroxide produced by a chemical or enzymatic reaction or to detect the presence of an enzyme which produces hydrogen peroxide, the process can be carried out in two different modes. In the first mode, the enzymatic reaction producing hydrogen peroxide using an enzyme such as glucose oxidase is carried out separately for a specified period of time under conditions optimized for that enzyme. A portion of the resulting solution is mixed with a reagent composition containing the hydroxyaryl cyclic diacylhydrazide and a peroxidase enzyme to produce the light. Alternately, both enzymatic reactions may be performed concurrently in one solution containing all of the components.

SPECIFIC DESCRIPTION

Nuclear magnetic resonance (NMR) spectra were obtained on a General Electric QE300 spectrometer as solutions in DMSO-$d_6$. Mass spectra were obtained on either a KRATOS MS-80 or an AEI MS-90 spectrometer. Chemiluminescence measurements were performed using either a TURNER TD-20e luminometer or a luminometer which is interfaced to an APPLE MACINTOSH computer running the LUMISOFT software package (Lumigen, Inc., Southfield, Mich.).

Solvents and reagents obtained from various commercial sources were the best available grade and were used without further purification unless noted otherwise. Enzymes were purchased from commercial sources and used without further purification.

1. Synthesis of Hydroxyaryl Cyclic Diacylhydrazides

5-Hydroxy-2,3-dihydrophthalazine-1,4-dione. 3-Hydroxyphthalic anhydride (2.0 g, 12.2 mmol, Aldrich) was stirred with 25 mL of glacial acetic acid until nearly all dissolved. Hydrazine (8.4 mL, 268 mmol) was added dropwise to the mixture. The reaction mixture fumed and became homogeneous with development of a yellow color. After a few minutes, a white precipitate formed and the yellow color faded. The mixture was stirred for three days and then filtered. The solids were washed with 150 mL of water followed by 125 mL of acetonitrile and allowed to dry in the air and then under vacuum. Yield: 2.06 g (95%). $^1$H NMR (DMSO-$d_6$): δ 12.83 (s, 1H), 12.06 (s, 1H), 11.68 (s, 1H), 7.76–7.70 (t, 1H), 7.34–7.31 (d, 1H), 7.14–7.12 (d, 1H); $^{13}$C NMR (DMSO-$d_6$): δ 163.04, 160.68, 152.74, 136.37, 126.38, 118.34, 114.50, 113.76; MS: (m/e) 178 ($M^+$), 148, 120, 92.

2. Chemiluminescent Detection of Peroxidase Enzymes

EXAMPLE 1

In the preferred method for practicing this invention the reagent solution for amplified detection of horseradish peroxidase consists of:

| Solution A | |
| --- | --- |
| Tris buffer, pH 8.8 | 0.1M |
| 5-hydroxy-2,3-dihydro-phthalazine-1,4-dione | $3.0 \times 10^{-3}$M |
| p-iodophenol | $4.8 \times 10^{-3}$M |
| Tween 20 | 1.0% (w/w) |
| Solution B | |
| Tris buffer, pH 8.8 | 0.1M |
| $NaBO_3 \cdot 4H_2O$ | $6.5 \times 10^{-3}$M |
| EDTA | $1 \times 10^{-4}$M |

The reagent is prepared by mixing solutions A and B in a 1:1 ratio. Enzyme solution: 5 μL of horseradish peroxidase 0.1 μg/mL.

Figure 1:
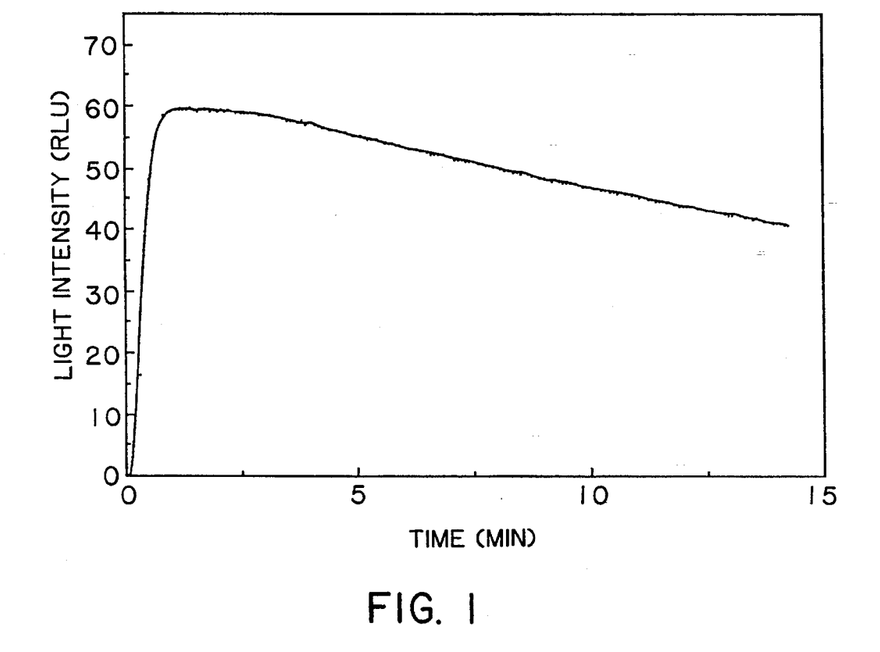
FIG. 1 is a graph of light intensity as a function of time from the horseradish peroxidase-initiated reaction of the hydroxyphthalhydrazide, 5-hydroxy-2,3-dihydrophthalazine-1,4-dione, of the present invention with hydrogen peroxide. The graph shows the light emitted from a 100 µL solution of 2 mM 5-hydroxy-2,3-dihydrophthalazine-1,4-dione, 3.3 mM $NaBO_3$, 2 mM p-phenylphenol, 0.1 mM EDTA and 0.17% Tween 20 in 0.1M pH 8.8 tris buffer, reacted with 5 ng of horseradish peroxidase.

Typically, 200 μL of the reagent was transferred into a polypropylene tube placed in a TURNER TD-20e or other suitable luminometer. The background luminescence was measured for a period of 5 minutes after which time a 5 μL aliquot of a horseradish peroxidase solution was added. FIG. 1 shows a plot of light intensity vs. time produced in this reaction at 25° C. This method allowed the measurement of as little as $6 \times 10^{-18}$ mol of horseradish peroxidase in 205 μL with a signal/background ratio of 4.

EXAMPLE 2

A reaction solution for amplified detection of horseradish peroxidase consists of:

| Solution A | |
| --- | --- |
| 2-Methyl-2-amino-1-propanol buffer, pH 9.8, 0.1M | |
| 5-hydroxy-2,3-dihydro-phthalazine-1,4-dione | $2.0 \times 10^{-3}$M |
| p-iodophenol | $2.0 \times 10^{-3}$M |
| Tween 20 | 0.167% (v/v) |
| $H_2O_2$ | 0.03% (w/w) |
| EDTA | $1 \times 10^{-4}$M |

Enzyme solution (5 μL of horseradish peroxidase 1 μg/mL) was injected into 3 mL of solution A.

Figure 2:
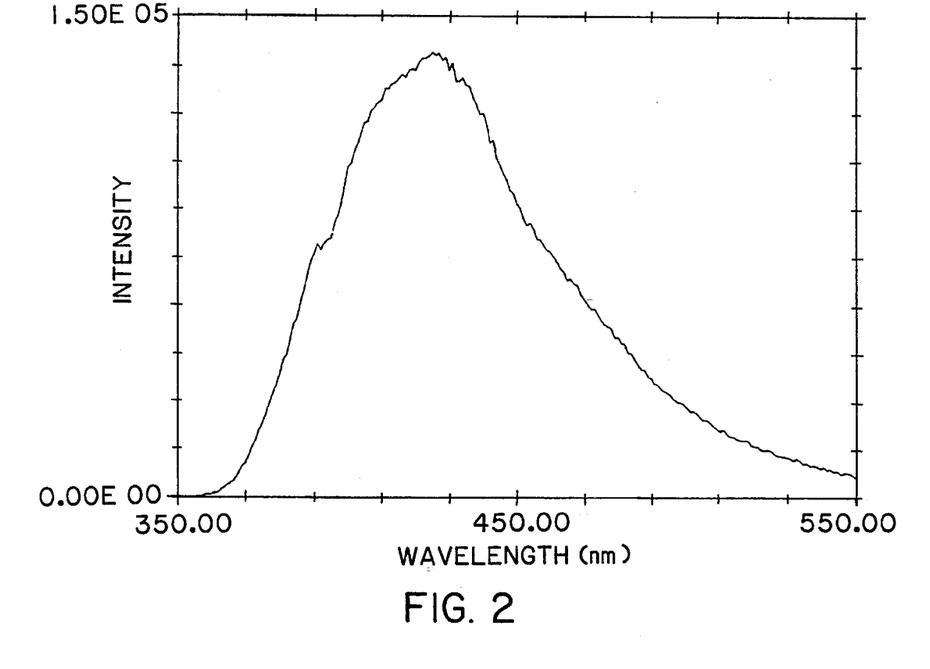
FIG. 2 is a graph of light intensity vs. wavelength from the horseradish peroxidase-initiated reaction of the hydroxyphthalhydrazides 5- and 6-hydroxy-2,3-dihydrophthalazine-1,4-dione of the present invention with hydrogen peroxide. The graph shows the light emitted from a 100 µL solution of 2 mM 5-hydroxy-2,3-dihydrophthalazine-1,4-dione, 0.003% $H_2O_2$, 2 mM p-iodophenol, 0.1 mM EDTA and 0.17% Tween 20 in 0.1M pH 9.8 2-methyl-2-amino-1-propanol (221) buffer reacted with 5 ng of horseradish peroxidase. The wavelength of maximum emission is 430 nm.

Chemiluminescence intensity rose to a maximum and remained at that level for > two hours. The spectrum showed maximal emission at 430 nm as demonstrated by FIG. 2.

EXAMPLE 3

A reaction solution for amplified detection of horseradish peroxidase consists of:

| Solution A | |
| --- | --- |
| 2-Methyl-2-amino-1-propanol buffer, pH 9.8, 0.1M | |
| 5-hydroxy-2,3-dihydrophthalazine-1,4-dione | $4.0 \times 10^{-3}$M |
| p-phenylphenol | $4.0 \times 10^{-3}$M |
| Tween 20 | 0.33% (v/v) |
| Solution B | |
| 2-Methyl-2-amino-1-propanol buffer, pH 9.8, 0.1M | |
| $H_2O_2$ | 0.006% (w/w) |
| EDTA | $2 \times 10^{-4}$M |

Figure 3:
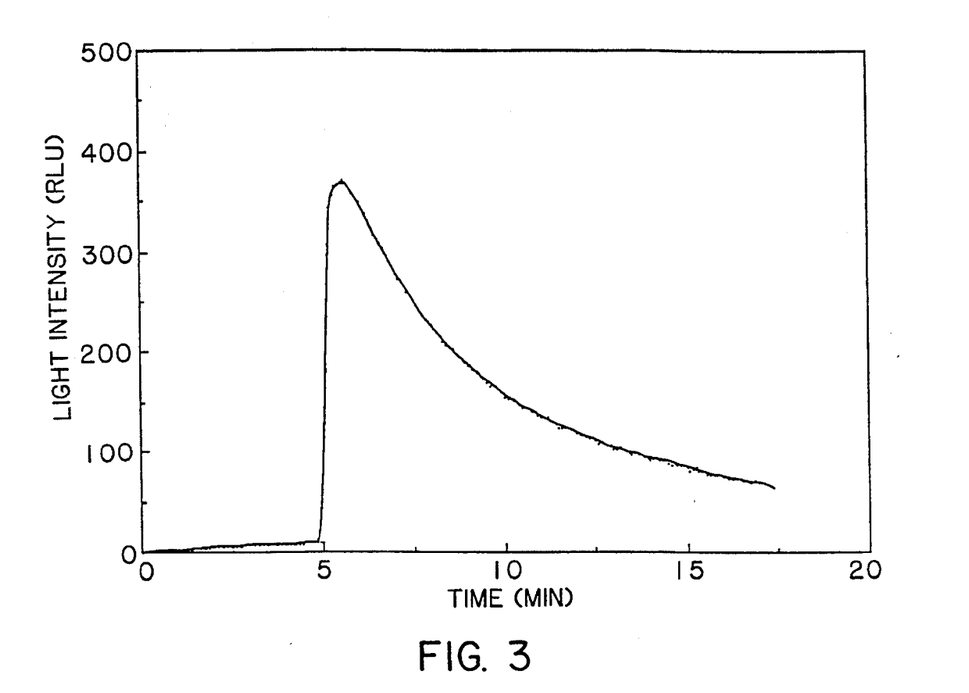
FIG. 3 is a graph of light intensity as a function of time from the horseradish peroxidase-initiated reaction of a phthalhydrazide of the present invention with hydrogen peroxide. The graph shows a sharp increase in the light emitted from a 100 µL solution of 2 mM 5-hydroxy-2,3-dihydrophthalazine-1,4-dione, 0.003% $H_2O_2$, 0.1 mM EDTA and 0.17% Tween 20 in 0.1M pH 8.8 tris buffer and 5 ng of horseradish peroxidase when 2 mM p-phenylphenol is added 5 minutes after the reaction is initiated.

The reagent is prepared by mixing solutions A and B in a 1:1 ratio. Enzyme solution (5 μL of horseradish peroxidase 1 μg/mL) was injected into 100 μL of the reaction solution. Chemiluminescence intensity increased sharply after addition of the phenolic compound (FIG. 3).

EXAMPLE 4

Figure 4:
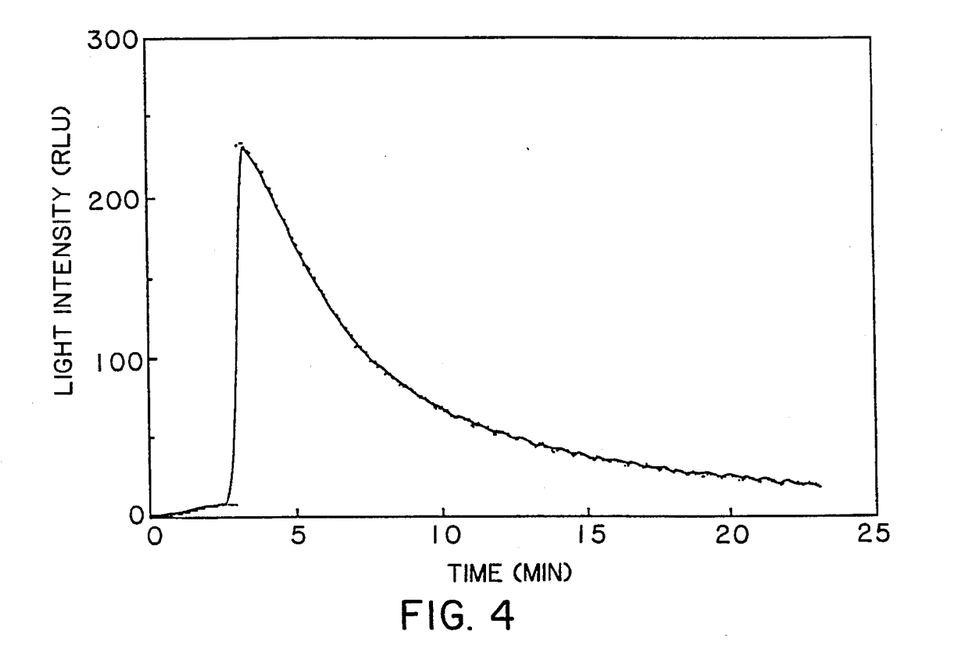
FIG. 4 is a graph of light intensity as a function of time from the horseradish peroxidase-initiated reaction of a phthalhydrazide of the present invention with hydrogen peroxide. The graph shows a sharp increase in the light emitted from a 100 µL solution of 2 mM 5-hydroxy-2,3-dihydrophthalazine-1,4-dione, 0.003% $H_2O_2$, 0.1 mM EDTA and 0.17% Tween 20 in 0.1M pH 8.8 tris buffer and 5 ng of horseradish peroxidase when 20 µM p-hydroxycinnamic acid is added 2.5 minutes after the reaction is initiated.

The solution used in Example 3 with the substitution of p-hydroxycinnamic acid ($2 \times 10^{-5}$M) for p-phenylphenol (FIG. 4). The results were similar.

EXAMPLE 5

Figure 5:
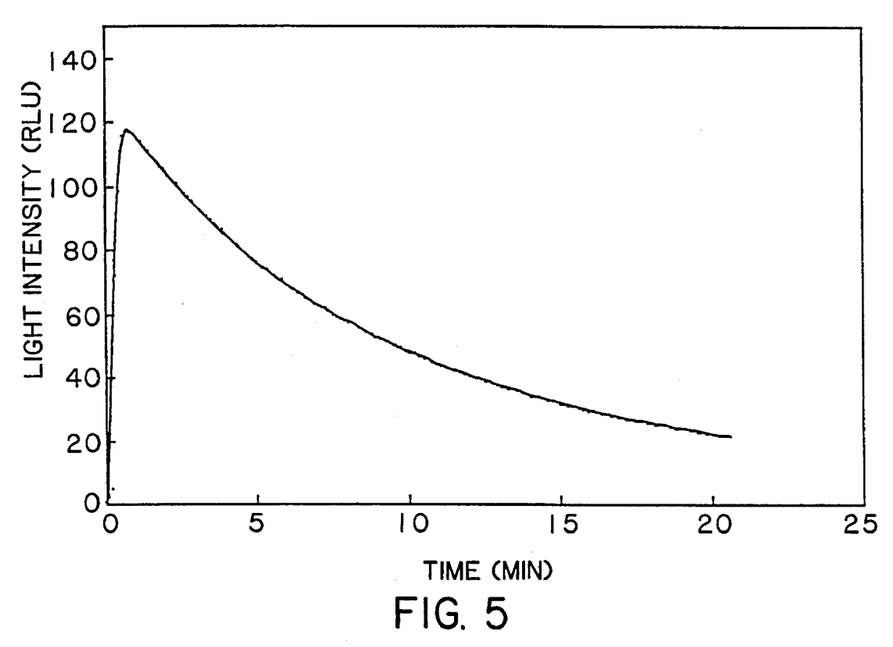
FIG. 5 is a graph of light intensity as a function of time from the horseradish peroxidase-initiated reaction of a phthalhydrazide of the present invention with hydrogen peroxide. The graph shows a sharp increase in the light emitted from a 100 µL solution of 2 mM 5-hydroxy-2,3-dihydrophthalazine-1,4-dione, 0.003% $H_2O_2$, 0.1mM EDTA and 0.17% Tween 20 in 0.1M pH 8.8 tris buffer and 5 ng of horseradish peroxidase when 2 mM 6-bromo-2-naphthol is added immediately after the reaction is initiated.

The solution used in Example 3 with the substitution of 6-bromo-2-naphthol for p-phenylphenol (FIG. 5). The results were similar.

EXAMPLE 6

Detection of hydrogen peroxide formed in the reaction of glucose with glucose oxidase.

Figure 6:
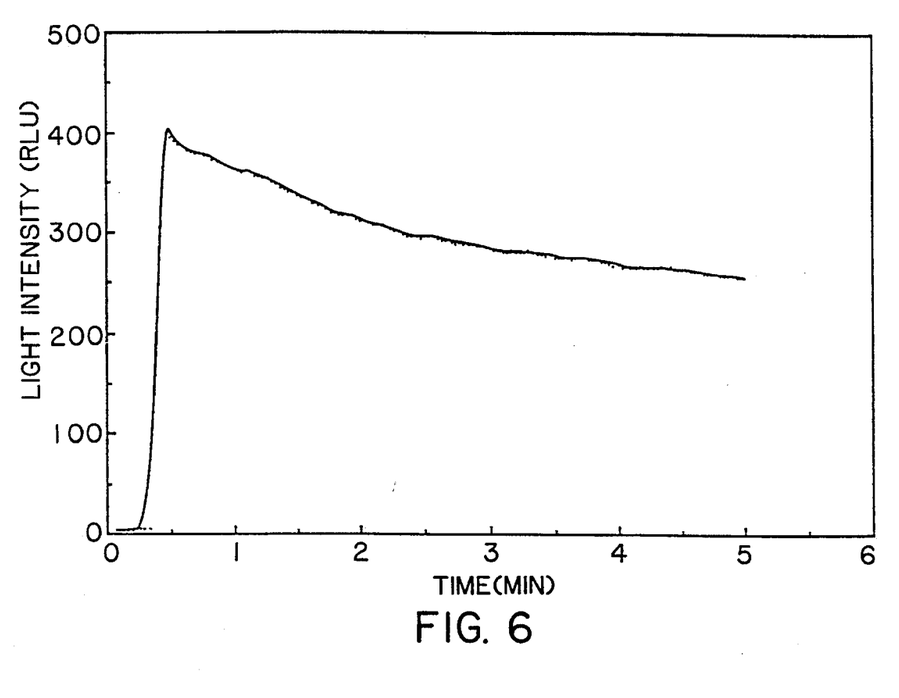
FIG. 6 is a graph of light intensity as a function of time from the reaction of a phthalhydrazide of the present invention with horseradish peroxidase, glucose oxidase and glucose. The graph shows the time profile of the light emitted from a 100 µL solution of 2 mM 5-hydroxy-2,3-dihydrophthalazine-1,4-dione, 2 mM p-phenylphenol, 0.1 mM EDTA and 0.17% Tween 20 in 0.1M pH 8.8 tris buffer and 5 ng of horseradish peroxidase. Chemiluminescence is produced after the reaction is initiated when a solution containing 0.01M glucose and 1.4 U of glucose oxidase which had been incubated for 15 minutes at room temperature is added at the point in the graph at approximately 0.3 minutes.

A solution of D-glucose (500 μL of 0.01M, 1.80 g/L) in water was incubated with 14 U of glucose oxidase (Biozyme Labs., San Diego, Calif.) for 15 minutes at 25° C. A 50 μL aliquot was injected into 50 μL of a 2× concentrate of the solution described in Example 1 containing horseradish peroxidase but without the hydrogen peroxide. The resulting chemiluminescence is depicted in FIG. 6. Control experiments established that emission of chemiluminescence was not initiated by addition of either glucose or glucose oxidase alone.

Repeating the experiment after overnight incubation of the glucose oxidase/glucose solution lead to a higher light intensity.

EXAMPLE 7

Detection of hydrogen peroxide formed in the reaction of glucose with glucose oxidase.

A solution of glucose oxidase (50 μL of 80 μg/mL) in buffer was injected into 100 μL of a solution consisting of:

| | |
|---|---|
| Tris buffer, pH 8.8 | 0.1M |
| D-glucose | $2 \times 10^{-2}$M to $2 \times 10^{-4}$M |
| 5-hydroxy-2,3-dihydrophthalazine-1,4-dione | $4.0 \times 10^{-3}$M |
| p-phenylphenol | $4.0 \times 10^{-3}$M |
| EDTA | $2 \times 10^{-4}$M |
| Tween 20 | 0.33% (v/v) |
| horseradish peroxidase (5 μL) | 10 mg/mL × 1/10,000 |

Figure 7:
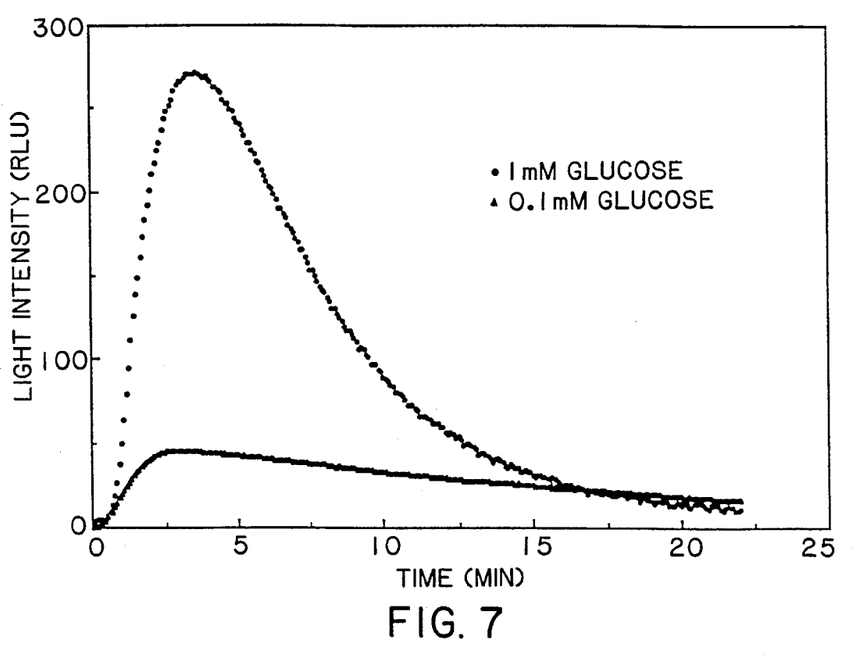
FIG. 7 is a graph of light intensity as a function of time from the reaction of a phthalhydrazide of the present invention with horseradish peroxidase, glucose oxidase and glucose. The graph shows the time profile of the light emitted from a 100 µL solution of 2 mM 5-hydroxy-2,3-dihydrophthalazine-1,4-dione, 2 mM p-phenylphenol, 0.1 mM EDTA and 0.17% Tween 20 in 0.1M pH 8.8 tris buffer, 5 ng of horseradish peroxidase, 1.4 U of glucose oxidase and either 1 mM or 0.1 mM glucose.

The resulting chemiluminescence which was produced on addition of glucose oxidase rose to a maximum and decayed slowly over a period of >1 hour as depicted in (FIG. 7).

EXAMPLE 8

Chemiluminescent Detection of DNA Dot Blots.

Immobilon-P membrane (Millipore, Bedford, Mass.) was sequentially soaked in methanol for 40 seconds, in $H_2O$ for two minutes and in 6xSSC (20xSSC is 3M NaCl, 0.3M sodium citrate, pH 7.0) for five minutes. The membrane was placed on two thicknesses of 3MM blotting paper (Whatman) containing 6xSSC. Biotinylated lambda DNA/Hind III fragments (Life Technologies, Inc., Bethesda, Md.) were diluted with 6xSSC containing 100 μg/mL sheared herring sperm DCNA (Boehringer-Mannheim, Indianapolis, Ind.) and 1.5 μL of each dilution of DNA was dotted on the Immobilon-P membrane or on nitrocellulose membrane (Schleicher & Schuell). Blots were air dried for 30 minutes and then baked for one hour at 80° C. Baked Immobilon-P was sequentially soaked in methanol for ten seconds, in $H_2O$ for two minutes and in 50 mM Tris-HCl buffered saline at pH 7.4 (TBS) for ten minutes. Baked nitrocellulose membrane was sequentially soaked in $H_2O$ for two minutes and in TBS for five minutes.

The membranes were blocked with 0.05% Tween-20 in Tris-HCl buffered saline at pH 7.4 (T-TBS) containing 1% non-fat milk (NFM) for one hour at room temperature with gentle agitation and then rinsed twice with T-TBS. Blots were incubated with a 1:10,000 dilution of avidin-horseradish peroxidase (Cappel Research Products) in T-TBS for 15 minutes at room temperature with gentle agitation. The membrane was then rinsed four times for 15 minutes each with T-TBS followed by four rinses with $H_2O$. Excess solution was removed from the membrane, the membrane was transferred to a fresh container and then incubated with the detection reagent solution described in Example 1 for five minutes. Excess detection reagent was drained off and the membrane was placed between transparency film (Arkwright, Inc.) Kodak X-OMAT XAR 5 film for 20 minutes.

The solutions A and B of Example 1 were used in this Example to produce chemiluminescence.

Figure 8A:
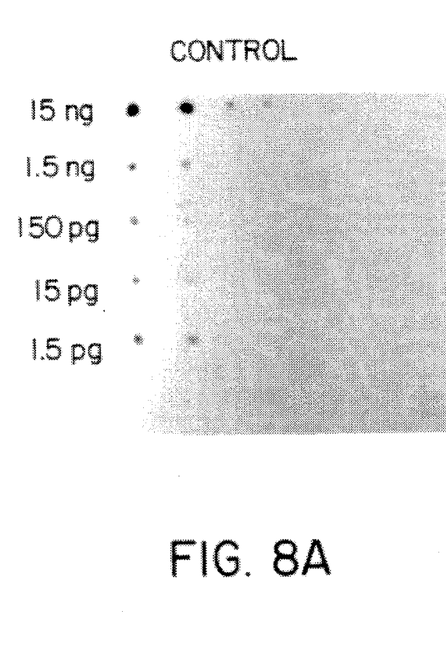
Figure 8B:
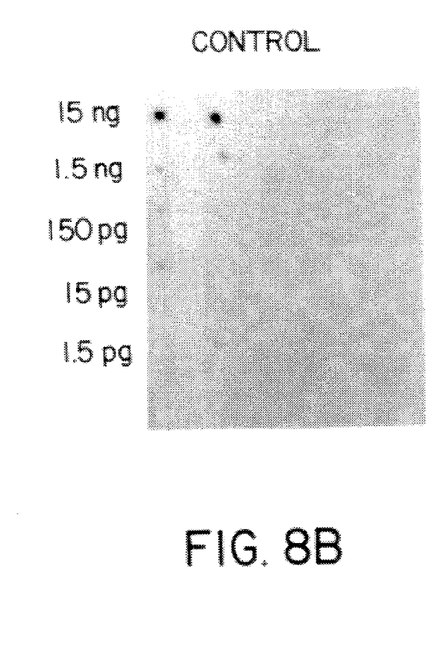

The DNA dot blots in FIG. 8 were performed with avidin-horseradish peroxidase and reagents of the present invention using (1) 15 ng, (2) 1.5 ng, (3) 150 pg, (4) 15 pg, (5) 1.5 pg and (6) 0 pg quantities of biotinylated lambda DNA/Hind III fragments each containing 150 ng herring sperm DNA. Spots of 15 ng biotinylated lambda DNA/Hind III fragments on nitrocellulose membrane produced stronger signals than the control spot containing 150 ng herring sperm DNA (FIG. 8A). The observed detection limit of at least 15 ng biotinylated lambda DNA dotted on nitrocellulose membrane was also obtained with dot blots on Immobilon-P using this detection reagent (FIG. 8B). Longer x-ray film exposures were required when using Immobilon-P with either detection reagent (data not shown) to achieve equivalent signal. The herring sperm DNA dot on the right of FIG. 8 represents non-specific binding of the labelled probe. The purpose of adding herring sperm DNA is that it is commonly used as a blocking agent in the hybridization procedures involved in nucleic acid hybridization assays and can be a source of non-specific binding which can limit assay sensitivity. The hydroxyaryl cyclic diacylhydrazides of the present invention can be coupled to biomolecules for use in probe and ELISA assays in the manner known to the prior art for the aminoaryl cyclic diacylhydrazides. The prior art cited in the application is exemplary of such methods.

It is intended that the foregoing description be only illustrative of the present invention and that the present invention be limited only by the hereinafter appended claims.

I claim:

1. A process for producing chemiluminescence which comprises reacting a hydroxyaryl cyclic diacylhydrazide with a peroxide compound, a phenolic enhancer compound and a peroxidase enzyme, wherein the hydroxyaryl has the formula HOAr.

2. A process for producing chemiluminescence which comprises reacting a hydroxyaryl cyclic diacylhydrazide of the formula:

with a peroxide compound, a phenolic enhancer compound and a peroxidase.

3. A process according to claim 2 wherein the hydroxyaryl cyclic diacylhydrazide is 5-hydroxy-2,3-dihydrophthalazine-1,4-dione.

4. A reagent composition which generates light in the presence of a peroxidase which comprises:

(a) a hydroxyaryl cyclic diacylhydrazide which generates light in the presence of a peroxidase;

(b) a phenolic compound which enhances light production from the diacylhydrazide;

(c) a peroxide compound which reacts with the peroxidase;

(d) a chelating agent which prevents the peroxide compound from reacting prior to addition of the peroxidase to the composition; and (e) a nonionic surfactant which acts to enhance the light production.

5. A reagent composition which generates light in the presence of a peroxidase which comprises:

(a) a hydroxyaryl cyclic diacylhydrazide of the formula:

(b) a phenolic compound which enhances light production;

(c) a peroxide compound which reacts with the peroxidase;

(d) a chelating agent which prevents the peroxide compound from reacting prior to addition of the peroxidase to the composition; and (e) a nonionic surfactant which acts to enhance the light production.

6. The reagent composition of claim 4 wherein the diacylhydrazide is 5-hydroxy-2,3-dihydrophthalazine-1,4 dione.

7. The reagent composition of any one of claims 4, 5 or 6 wherein the chelating agent is ethylenediamine tetraacetic acid salt (EDTA).

8. The reagent composition of any one of claims 4, 5 or 6 wherein the chelating agent is EDTA and wherein the phenolic compound is selected from the group consisting of p-phenylphenol, p-iodophenol, p-bromophenol, p-hydroxycinnamic acid and 2-cyano-6-hydroxybenzothiazole.

9. The reagent composition of any one of claims 4, 5 or 6 wherein a molar ratio of phenolic compound to diacylhydrazide is between about 0.001 and 4 wherein a molar ratio of peroxide compound to diacylhydrazide is between about 0.01 and 2, wherein a molar ratio of chelating agent to diacylhydrazide is between about 0.01 and 2, and wherein the amount of surfactant is between about 0.01 and 1% by weight.

10. In a method for detecting an analyte in an assay selected from the group consisting of a nucleic acid-hybridization assay and an enzyme-linked immunoassay procedure by a chemiluminescent reaction, the improvement which comprises reacting a hydroxyaryl cyclic diacylhydrazide of the formula:

with a peroxide compound, a phenolic enhancer compound and a peroxidase to thereby produce light for detecting the analyte.

11. The method of claim 10 wherein the diacylhydrazide is 5-hydroxy-2,3-dihydrophthalazine-1,4-dione.

12. In a method for detecting an analyte in an assay selected from the group consisting of a nucleic acid-hybridization assay and an enzyme-linked immunoassay procedure by a chemiluminescent reaction, the improvement which comprises:

(a) providing a reagent composition which generates light in the presence of a peroxidase which comprises: a hydroxyaryl cyclic diacylhydrazide; a phenolic compound which enhances light; a peroxide compound which reacts with the peroxidase; a chelating agent which prevents the peroxide compound from reacting prior to the addition of the peroxidase to the composition; and a nonionic surfactant which acts to enhance the light production; and (b) adding a peroxidase to the reagent composition so that light is produced for detecting the analyte.

13. The method of claim 12 wherein the peroxidase enzyme is coupled to an analyte binding compound which specifically binds to the analyte.

14. The method of claim 13 wherein the analyte binding compound to which the peroxidase is coupled is selected from the group consisting of antibodies, oligonucleotides, haptens, and proteins.

15. The method of any one of claims 11, 12, 13 or wherein the chelating agent in the reagent composition is EDTA.

16. The method of any one of claims 11, 12, 13 or 14 wherein the phenolic compound in the reagent composition is selected from the group consisting of p-phenylphenol and p-iodophenol.

17. The method of any one of claims 11, 12, 13 or 14 wherein the phenolic compound in the reagent composition is selected from the group consisting of p-phenylphenol and p-iodophenol and the chelating agent is EDTA.

18. The method of any one of claims 13 or 14 wherein the detection is performed on a membrane.

19. The method of claim 18 wherein the membrane is selected from the group consisting of a nitrocellulose, nylon and polyvinylidene difluoride membranes.

20. The method of any one of claims 13 or 14 wherein the chemiluminescence produced is detected on photographic film.

21. The method of any one of claims 13 or 14 wherein the chemiluminescence produced is detected by a luminometer.

22. A kit for detecting an analyte in an assay procedure by a chemiluminescent reaction to produce light which comprises in separate containers:

(a) a hydroxyaryl cyclic diacylhydrazide and a phenolic compound which enhances light production in a reagent composition; and (b) a peroxidase enzyme, wherein the light is detected in the assay proceduce by reacting the reagent composition with the peroxidase.

23. A kit for detecting an analyte in an assay procedure by a chemiluminescent reaction to produce light which comprises in separate containers:

(a) a hydroxyaryl cyclic diacylhydrazide of the formula and a phenolic compound which enhances light production in a reagent composition; and

(b) a peroxidase enzyme, wherein the light is detected in the assay proceduce by reacting the reagent composition with the peroxidase.

24. A kit for detecting an analyte in an assay procedure by a chemiluminescent reaction to produce light which comprises in separate containers:

(a) 5-hydroxyphenyl-2,3-dihydrophthalazine-1,4-dione and a phenolic compound which enhances light production in a reagent composition; and (b) a peroxidase enzyme, wherein the light is detected in the assay proceduce by reacting the reagent composition with the peroxidase.

25. A kit for detecting an analyte in an assay procedure by a chemiluminescent reaction to produce light which comprises in separate containers:
  (a) a reagent composition which generates light in the presence of a peroxidase which comprises: a hydroxyaryl cyclic diacylhydrazide of the formula:

a phenolic compound which enhances light production; a peroxide compound which reacts with the the peroxidase, a chelating agent which prevents the peroxide compound from reacting prior to the addition of the peroxidase to the composition; and a nonionic surfactant which acts to enhance the light production; and
  (b) a peroxidase enzyme, wherein the light is detected in the assay procedure by reacting the reagent composition with the peroxidase.

26. A kit for detecting an analyte in an assay procedure by a chemiluminescent reaction to produce light which comprises in separate containers:
  (a) a reagent composition which generates light in the presence of a peroxidase which comprises: 5-hydroxy-2,3-dihydrophthalazine-1,4-dione; a phenolic compound which enhances light production from the diacylhydrazide; a peroxide compound which reacts with the diacylhydrazide in the presence of the peroxidase; a chelating agent which prevents the peroxide compound from activating the diacylhydrazide prior to the addition of the peroxidase to the composition; and a nonionic surfactant which acts to enhance the light production; and
  (b) a peroxidase enzyme, wherein the light is detected in the assay procedure by reacting the reagent composition with the peroxidase.

27. In a method for detecting hydrogen peroxide in an assay selected from the group consisting of a nucleic acid-hybridization assay and an enzyme-linked immunoassay procedure by a chemiluminescent reaction, the improvement which comprises reacting hydrogen peroxide with a hydroxyaryl cyclic diacylhydrazide of the formula:

a phenolic enhancer compound and a peroxidase enzyme to produce light.

28. The method of claim 27 wherein the diacylhydrazide is 5-hydroxy-2,3-dihydrophthalazine-1,4-dione and the peroxidase enzyme is selected from the group consisting of horseradish peroxidase, microperoxidase and lactoperoxidase.

29. In a method for detecting peroxidase enzymes in an assay selected from the group consisting of a nucleic acid-hybridization assay and an enzyme-linked immunoassay procedure by a chemiluminescent reaction, the improvement which comprises reacting a peroxide, a phenolic enhancer compound and a hydroxyaryl cyclic diacylhydrazide of the formula:

with a peroxidase enzyme to produce light.

30. The method of claim 29 wherein the diacylhydrazide is 5-hydroxy-2,3-dihydrophthalazine-1,4-dione and the peroxide is selected from the group consisting of hydrogen peroxide and perborate salts.

* * * * *

UNITED STATES PATENT AND TRADEMARK OFFICE
CERTIFICATE OF CORRECTION

PATENT NO. : 5,552,298
DATED : September 3, 1996
INVENTOR(S) : Hashem Akhavan-Tafti

It is certified that error appears in the above-indentified patent and that said Letters Patent is hereby corrected as shown below:

Column 14, line 13 (Claim 15), "Claims 11, 12, 13 or" should read --Claims 11, 12, 13 or 14--.

Column 15, line 16 (Claim 25), delete "the", second occurrence.

Signed and Sealed this

Fourteenth Day of January, 1997

Attest:

BRUCE LEHMAN

Attesting Officer

Commissioner of Patents and Trademarks